United States Patent [19]

Wilkinson et al.

[11] Patent Number: 4,504,492

[45] Date of Patent: Mar. 12, 1985

[54] PHARMACEUTICAL AMIDES, AND PREPARATION, FORMULATIONS AND USE THEREOF

[75] Inventors: Samuel Wilkinson, Beckenham; George W. Hardy, Biggin Hill, both of England

[73] Assignee: Burroughs Wellcome Co., Research Triangle Park, N.C.

[21] Appl. No.: 422,997

[22] Filed: Sep. 24, 1982

[30] Foreign Application Priority Data

Sep. 25, 1981 [GB] United Kingdom ............... 8129053

[51] Int. Cl.³ ............... A61K 31/275; A61K 31/215; A61K 31/195; C07C 101/24
[52] U.S. Cl. ............... 514/522; 260/465 B; 260/465 D; 260/465 E; 514/534; 514/603; 514/616; 560/13; 560/16; 560/22; 560/39; 562/426; 562/430; 562/437; 562/448; 564/82; 564/86; 564/153
[58] Field of Search ............... 562/450, 426, 430, 432, 562/437, 448; 424/319, 304, 309, 324; 560/13, 15, 18, 22, 37, 39, 41, 42; 564/153; 260/465 D, 465 E, 465 B

[56] References Cited

U.S. PATENT DOCUMENTS

| | | | |
|---|---|---|---|
| 4,105,789 | 8/1978 | Ondetti et al. | 562/450 |
| 4,228,184 | 10/1980 | Ondetti et al. | 562/450 |
| 4,386,031 | 5/1983 | Hillboll et al. | 424/319 X |
| 4,423,242 | 12/1983 | Wilkinson et al. | 560/22 X |

FOREIGN PATENT DOCUMENTS

| | | | |
|---|---|---|---|
| 0038758 | 10/1981 | European Pat. Off. | 424/319 |
| 0082088 | 6/1983 | European Pat. Off. | |
| 2074571 | 11/1981 | United Kingdom | 560/41 |

OTHER PUBLICATIONS

*European Journal of Pharmacology*, vol. 57, pp. 279-281, (1979), Swerts et al.
*Nature*, vol. 258, pp. 577-579, (1975), Hughes et al.
*Nature*, vol. 276, pp. 523-526, (1978), Malfroy et al.

Primary Examiner—Natalie Trousof
Assistant Examiner—Patricia M. Scott
Attorney, Agent, or Firm—Donald Brown

[57] ABSTRACT

Compounds of the general formula

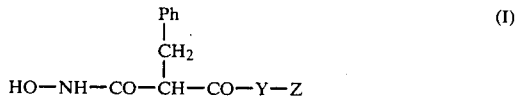

wherein Ph is a phenyl group which is optionally substituted by one or more substituents selected from halo (i.e. fluoro, chloro, bromo or iodo), $C_{1-4}$alkyl, amino, $C_{1-4}$alkylamino, di-$C_{1-4}$alkylamino, nitro, sulphonyl, aminosulphonyl, trihalomethyl, carboxy, $C_{1-4}$alkoxycarbonyl, amido, $C_{1-4}$alkylamido, $C_{1-4}$alkoxy, $C_{2-4}$alkenyl, cyano, aminomethyl, or methylsulphonyl; Y is a group of formula

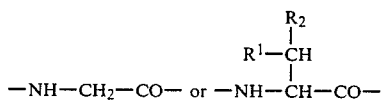

where $R^1$ is hydrogen or methyl; $R^2$ is alkyl of 1 to 3 carbon atoms or is methylthiomethyl; and Z is $-OR^3$ or $-NR^4R^5$ where $R^3$, $R^4$ and $R^5$ are each hydrogen or alkyl of 1 to 4 carbon atoms and $R^3$ can further be phenylalkyl having 1 to 3 carbon atoms in the alkylene moiety thereof, or phenyl; and basic salts thereof. These compounds have an advantageous enkephalinase inhibitory activity which renders the compounds useful in medical therapy, e.g. to prolong and/or potentiate in a mammal, the effects of endogenous or exogenous enkephalins. The latter includes synthetic enkephalin analogues.

13 Claims, No Drawings

PHARMACEUTICAL AMIDES, AND PREPARATION, FORMULATIONS AND USE THEREOF

This invention relates to amides and their preparation, to pharmaceutical formulations containing such compounds and the preparation of such formulations, to the use of such compounds in human and veterinary medicine, and to intermediates of value in the preparation of the amides and the preparation of such intermediates.

In 1975, Hughes et al. (*Nature* Vol. 258, Dec. 18, 1975 pages 577 to 579) identified two related pentapeptides from the mammalian brain with potent opiate agonist activity, the enkephalins:

H.Tyr.Gly.Gly.Phe.Met.OH(Met$^5$-enkephalin)

H.Tyr.Gly.Gly.Phe.Leu.OH(Leu$^5$-enkephalin).

(The abbreviations used herein for amino acids and their radicals are those conventional in the art and may be found in, for example, *Biochemical Journal* (1972) 126, pages 773 to 780. In the above and throughout the following all references are to the L-configuration of chiral amino acids and their radicals unless otherwise stated).

Since this discovery the enkephalins have been studied by a number of workers and from a variety of approaches. One such approach concerns investigation of their inactivation and recent reports (for example Malfroy et al. *Nature* Vol. 276, 30 Nov. 1978 pages 523 to 526 and Gorenstein et al., *Life Sciences* Vol. 25 (1979) pages 2065 to 2070) have indicated that there exists in mammalian brain a dipeptidylcarboxypeptidase ("enkephalinase") capable of hydrolysing the Gly$^3$Phe$^4$ bond H.Tyr.Gly.Gly.Phe.$^{Met}_{Leu}$.OH Enkephalinase thus has a role in some ways comparable with that of the mammalian angiotensin converting enzyme (ACE, EC, 3.4.15.1) which acts upon the relatively inactive decapeptide angiotensin I.

H.Asp.Arg.Val.Tyr.$^{Val}_{Ile}$His.Pro.Phe.His.Leu.OH at the Phe$^8$—His$^9$ bond to release the potent pressor octapeptide angiotensin II.

H.Asp.Arg.Val.Tyr.$^{Val}_{Ile}$His.Pro.Phe.OH although it has been demonstrated (Swerts et al, *European Journal of Pharmacology* Vol. 57 (1979) pages 279 to 281) that the two enzymes are distinct species.

Controlling the liberation of angiotensin II from angiotensin I, by selectively inhibiting ACE, has for some time been regarded as a possible method for the therapy of hypertension and a number of agents, originating from such an approach and exhibiting the desired properties, have been described. One especially potent compound is 1-(D-3-mercapto-2-methylpropanoyl)-L-proline (S,S), otherwise known as Captopril or SQ 14 225 and having the structure $$HS.CH_2.CH(CH_3).CO.N\langle\text{pyrrolidine}\rangle CO_2H$$

This has been reported as capable of inhibiting both enkephalinase and ACE (Swerts et al, Loc. cit.) but as having a far greater specificity for the latter enzyme than for the former, the concentration of compound required to inhibit ACE by 50% being approximately 1000-fold lower than that required to effect the same degree of inhibition enkephalinase.

Published European patent application No. EP 0 038 758 A1 (Roques, Schwartz and Lecomte) describes amino-acid derivatives, said to be capable of inhibiting enkephalinase, in particular, there is disclosed a compound 'Thiorphan' which has the formula $$HS-CH_2-CH(CH_2Ph)-CO-NH-CH_2-CO_2H$$

(DL-3-mercapto-2-benzylpropanoyl)-glycine.

The present invention relates to a class of compound which have not only an advantageous enkephalinase inhibitory activity but also, in distinction to SQ 14 225, a greater specificity for enkephalinase than for ACE.

The present invention thus provides the amides of formula (I)

$$HO-NH-CO-CH(CH_2Ph)-CO-Y-Z \quad (I)$$

together with basic salts thereof (i.e. salts formed by reaction of a compound of formula (I) with a base), wherein Ph is a phenyl group which is optionally substituted by one or more substituents selected from halo (i.e. fluoro, chloro, bromo or iodo), $C_{1-4}$ alkyl, amino, $C_{1-4}$ alkylamino, di-$C_{1-4}$ alkylamino, nitro, sulphonyl, aminosulphonyl, trihalomethyl, carboxyl, $C_{1-4}$ alkoxycarbonyl, amido, $C_{1-4}$ alkylamido, $C_{1-4}$ alkoxy, $C_{2-4}$ alkenyl, cyano, aminomethyl or methylsulphonyl.

Y is a group of formula:

$$-NH-CH_2-CO- \text{ or } -NH-CH(CH(R^1)R^2)-CO-$$

where $R^1$ is hydrogen or methyl;

$R^2$ is alkyl of 1 to 3 carbon atoms or is methylthiomethyl; and

Z is $-OR^3$ or $-NR^4R^5$ where $R^3$, $R^4$ and $R^5$ are each hydrogen or alkyl of 1 to 4 carbon atoms and $R^3$ can further be phenylalkyl having 1 to 3 atoms in the alkylene moiety thereof or phenyl.

Formula (I) as above defined includes a plurality of asymmetric centers and should be understood to include all optical isomers embraced thereby and mixtures thereof.

In some instances described below (Examples 4(b) and 5(b)), where an intermediate stage of preparation of a particular compound of formula (I) entails crystallisation of an ester from an ether/dicylochexylamine (DCHA) solution, fractional crystallisation permits partial resolution of the diastereomers in respect of one of the asymmetric centres. In these examples, isomerism with respect to the other at the asymmetric centres is predetermined.

In the salts of the amides of formula (I) the pharmacological activity resides in the amide (acid) anion and the identity of the cation is of less importance although for therapeutic purposes it is preferably pharmacologically and pharmaceutically acceptable to the recipient. Acceptable salts include ammonium salts, alkali metal salts such as lithium, sodium and potassium salts, alkaline earth metal salts such as magnesium and calcium salts, and salts of organic bases, for example amine salts derived from mono-, di- or trilower alkylamines or cycloalkylamines such as dicyclohexylamine or alkanolamines such triethanolamine and diethylaminoethylamine and salts with heterocyclic amines such as piperidine, pyridine, piperazine and morpholine.

As subclasses of the amides of formula (I), may be mentioned, are those of the amides of formula (I) wherein:

(i) Ph is unsubstituted phenyl or phenyl substituted by iso-propyl, methoxy, nitro or bromo, in particular in the 4-position;

(ii) Y is a group of formula

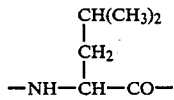

(in either the D- or the L-configuration).

(iii) Y is a group of formula

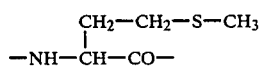

(in either the D- or the L-configuration).

(iv) Y is a group of formula —NH—CH$_2$—CO—;

(v) R$^3$ is an ethyl, methyl, n-propyl, isopropyl, n-butyl, isobutyl or t-butyl group, in particular a methyl, ethyl or t-butyl group;

(vi) R$^3$ is hydrogen.

The amides of formula (I) and their basic salts may be prepared by any of the methods known in the art for the preparation of compounds of analogous structure. Thus they may be prepared by reacting a compound of formula

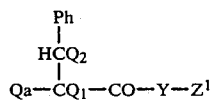

(wherein Ph and Y are as defined in formula (I),

Q$_a$ is carboxy or a functional equivalent thereof;

Q$_1$ and Q$_2$ are both hydrogen or together form a bond; and

Z$^1$ is a group Z as defined in formula (I) or a functionally protected derivative thereof with hydroxylamine or a functionally protected O-derivative thereof (e.g. O-benzylhydroxylamine); followed (when Q$^1$ and Q$^2$ together form a bond) by selective reduction of the said bond and, as appropriate, by deprotection of the product and conversion of the product into the amide or a basic salt thereof.

The reaction of the compound of formula (II) with hydroxylamine or the above mentioned derivative thereof, may be effected, for example, according to the following preferred embodiments:

(a) reaction of hydroxylamine with a compound of formula (II) wherein Q is a carboxy group and Z$^1$ is a functionally protected derivative of the group Z, for example, a tert-butoxy protecting group, followed by removal of the protecting group for Z, e.g. using trifluoroacetic acid to convert the tert-butoxy protecting group to a hydroxy group; or (b) reaction of a compound of formula (II), as defined in (a) above, with a functionally protected O-derivative of hydroxylamine, e.g. O-benzylhydroxylamine, followed, as in (a) above, by removal of the protecting group for Z and also removal of the protecting group for the hydroxamate group e.g. by hydrogenation in the presence of palladium/charcoal to remove the above-mentioned benzyl protecting group.

The reaction of the compound of formula (II) with hydroxylamine or the above-mentioned derivative thereof may be effected in a conventional manner, e.g. using the mixed anhydride procedure.

The compound of formula (II) above may be prepared in conventional manner, e.g. by reaction of a compound of formula

(wherein Ph, Q$_1$, Q$_2$ and Q$_a$ are as defined in formula (II) and Q$_b$ is carboxyl or a functional equivalent thereof) with a compound of formula

(wherein Y and Z$^1$ are as defined in formula (II)) followed, as desired, by (a) selective reduction of the Q$^1$-Q$^2$ bond (when Q$^1$ and Q$^2$ together form a bond) and (b) removal of protecting groups.

The reaction of (III) with (IV) may be effected using techniques standard in peptide chemistry and using either classical methods of peptide synthesis or solid phase procedures. Details of suitable activating and protecting groups and of suitable reaction conditions (both for the reaction of (III) and (IV) and for the removal of protecting groups) may be found in the following literature which is given purely by way of exemplification and which is intended to be neither exhaustive nor limiting:

(a) Schroder and Luebke, "The Peptides" (Academic Press) (1965).

(b) Bellean and Malek, *J.Am.Chem.Soc.*, 90, 165 (1968).

(c) Tilak. *Tetrahedron Letters*, 849 (1970).

(d) Beyerman, *Helv.Chim.Acta.*, 56, 1729 (1973).

(e) Stewart and Young, "Solid Phase Peptide Synthesis" (W. H. Freeman and Co.) (1969)

Certain of the amides of formula (I) may also be prepared from precursors which are themselves within formula (I).

Thus, (i) compounds wherein Z is —OH where $R^3$ is hydrogen may be prepared by hydrolysis of corresponding compounds where $R^3$ is alkyl, phenylalkyl or phenyl;

(ii) compounds wherein Z is —$OR^3$ where $R^3$ is alkyl, phenylalkyl or phenyl may be prepared by esterification of the corresponding compound where $R^3$ is hydrogen;

(iii) compounds wherein Z is —$NR^4R^5$ may be prepared by reaction of a corresponding compound wherein Z is —$OR^3$ where $R^3$ is alkyl, phenylalkyl or phenyl with as appropriate ammonia or a mono- or dialkylamine.

The amides of formula (I) may be converted into basic salts thereof and the converse, by well established techniques.

When $Q_1$ and $Q_2$ in formula (II) both represent hydrogen, the compound of formula (III) may be prepared for example by the reaction of a malonic acid diester (e.g. the diethyl ester) with an appropriate benzyl halide of formula

(where Ph is as defined in formula (II) and Hal is halo e.g. bromo) followed by deprotection as desired to obtain the compound of formula (III).

When the preparative procedures hereinabove described provide a mixture of optical isomers of the amide of formula (I) or of an intermediate thereto, for example a mixture of diastereoisomers, the individual isomers may be separated by appropriate conventional physical techniques such as high performance liquid chromatography, preparative thin layer chromatography and the like.

Because of their selective enkephalinase-inhibiting activity the amides of formula (I) and the basic salts thereof are of value in the in vitro and in vivo investigation of the mode of action and role of the enzyme and in its localization, isolation and purification.

For example, the present invention provides a method which comprises contacting an amide of formula (I) or a basic salt thereof with enkephalinase and determining the inhibitory effect of the amide or salt on the enzyme activity of the enkephalinase. This method can be used to compare the enkephalinase inhibitory effect of the above compounds with other compounds having a similar effect. The compounds according to the invention can be radiolabelled, if desired, to facilitate the determination of their inhibitory effect.

Their selective enkephalinase-inhibiting activity also confers on the amides of formula (I) and the pharmacologically and pharmaceutically acceptable basic salts thereof, utility in the prolongation and potentiation in a mammal of the effects of enkephalins of either endogenous or exogenous origin including in the latter case synthetic enkephalin analogues. The said amides and salts thus have the same activities and utilities as have been indicated for the endogenous compounds.

The amides of formula (I) may therefore be useful for the prophylaxis and/or treatment of anxiety in mammals such as man, e.g. by virtue of an ability to induce tranquillization.

The amides of formula (I) may also be useful for the prophylaxis and/or treatment of convulsions in mammals such as man.

A recent study (G. E. Sander et al., Peptides Vol. 2 (1981) pp 403–407) has suggested a role for enkephalins in cardio-pulmonary function. The amides of formula (I) may therefore also be useful for the prophylaxis and/or treatment of a condition of a mammal such as man, wherein an improvement in cardio-pulmonary function is indicated, for example to relieve dyspnoea, e.g. that of acute left ventricular failure or pulmonary oedema.

Furthermore, the amides of formula (I) and the pharmacologically and pharmaceutically acceptable basic slats thereof have morphinomimetic (morphine agonist) activity and thus may be used in the treatment of mammals in the fields of both human and veterinary medicine in any condition where an agent with a morphine-like effect is indicated.

The pharmacological properties and therapeutic uses of morphine are well documented in the literature (see for example *The Pharmacological Basis of Therapeutics* Goodman, L. S. and Gilman, A. eds., published by Macmillan Publishing Co., Inc., New York, fifth edition (1975), ISBN 0-02-344781-8, especially at Chapter 15 pages 245 to 283, and *Martindale: The Extra Pharmacopoeia*, Wade. A. ed., published by the Pharmaceutical Press, London, twenty-seventh edition (1977), ISBN 0-85369-114-2, especially at pages 970 to 974) and specific utilities for the said amides and salts include, by way of example, the following:

(1) The relief of pain (analgesia), for example pain arising from spasm of smooth muscle as in renal or biliary colic, pain in terminal illness such as terminal cancer, pain in the postoperative period, and obsterical pain.

(2) The induction of constipation, for example after ileostomy of colostomy.

(3) The treatment of diarrhoea or dysentery.

(4) The suppression of cough.

(5) The induction of sleep, especially where sleeplessness is due to pain or cough.

(6) Sedation, for example in pre-anaesthetic medication to reduce preoperative apprehension.

(7) The induction of euphoria and the treatment of depression, for example when allied to the relief of pain in terminal illness such as terminal cancer.

The amides of formula (I) and the pharmacologically acceptable basic salts thereof (hereinafter collectively referred to as the active ingredients) may be administered to the human or non-human recipient by any route appropriate to the condition to be treated, suitable routes including oral, rectal, nasal, topical (including buccal and sublingual), vaginal and parenteral (including subsutaneous, intramuscular, intravenous, intradermal, intrathecal and epidural). It will be appreciated that the preferred route may vary with for example the condition of the recipient.

For each of the above-indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilities and indications, a suitable, effective dose, will be in the range 0.075 µg to 12 mg per kilogram bodyweight of recipient (human or non-human) per day, preferably in the range 0.75 µg to 1.2 mg per kilogram bodyweight per day and most preferably in the range 7.5 to 120 µg per kilogram bodyweight per day; an optimum dose is 30 µg per kilogram bodyweight per day. (Unless otherwise indicated all weights of active ingredient are calculated as the amide of formula (I): for salts thereof the figures would be increased proportionately.) The desired dose is preferably presented as between two and four sub-doses and each will generally lie in the range 0.025 μg to 4 mg, preferably 0.25 μg to 0.4 mg and most preferably 2.5 to 40 μg per kilogram bodyweight with an optimum of 10 μg per kilogram bodyweight. A daily dose for a human weighing of the order of 50 kg will thus generally lie in the range 3.75 μg to 600 mg, preferably in the range 37.5 μg to 60 mg and most preferably in the range 0.375 to 6.0 mg and may conveniently be presented as three equal unit sub-doses of 1.25 μg to 200 mg, preferably 12.5 μg to 20 mg and most preferably 0.125 to 2.0 mg. Optimally a human daily dose, for an individual weighing of the order of 50 kg, is 1.5 mg conveniently presented as three unit sub-doses each of 0.5 mg.

While it is possible for the active ingredients to be administered as the raw chemical it is preferable to present them as a pharmaceutical formulation preparation. The formulations, both veterinary and for human use, of the present invention comprise an active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulation for rectal administration may be presented as a suppository with the usual carriers such as cocoa butter.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder hald close up to the nose. Suitable formulations wherein the carrier is a liquid, for administration as for example a nasal spray or as nasal drops, include aqueous or oily solutions of the active ingredient.

Formulations suitable for topical administration in the mouth include lozenges comprising the active ingredient in a flavoured basis, usually sucrose and acacia or tragacanth; and pastilles comprising the active ingredient in an inert basis such as gelatin and glycerin, or sucrose and acacia.

Formulations suitable for vaginal administration may be presented as pessaries, creams, pastes or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented to unit-dose or multidose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as hereinabove recited, or an appropriate fraction thereof, of an active ingredient.

It should be understood that in addition to the ingredients particularly mentioned above the formulations of this invention may include other agents conventional in the art having regard to the type of formula in question, for example those suitable for oral administration may include flavouring agents.

All references identified hereinabove or in the following are hereby incorporated herein by reference thereto.

Those basic salts which are not pharmacologically and pharmaceutically acceptable may be converted to the amides themselves and to salts thereof which are acceptable by standard procedures.

It will be understood from the foregoing description that this invention may comprise any novel feature described herein, principally but not exclusively for example:

(a) Amides of formula (I) as hereinbefore defined and the basic salts thereof.

(b) Methods as hereinbefore described for the preparation of compounds according to (a) supra, together with the compounds when so prepared.

(c) A pharmaceutical formulation comprising a therapeutically effective amount of an amide of formula (I) as hereinbefore defined or a pharmacologically and pharmaceutically acceptable basic salt thereof together with an acceptable carrier therefor.

(d) A method for the preparation of a formulation according to (c) supra comprising admixture of the active ingredient, as defined, with the carrier therefor.

(e) Amides of formula (I) as hereinbefore defined and pharmacologically and pharmaceutically acceptable basic salts thereof, for use in the therapeutic treatment of a mammal.

(f) Amides of formula (I) as hereinbefore defined and pharmacologically and pharmaceutically acceptable basic salts thereof, for use in the therapeutic treatment of a human.

(g) Amides of formula (I) as hereinbefore defined and pharmacologically and pharmaceutically acceptable basic salts thereof, for use in prolongation and/or potentiation in a mammal of the effects of endogenous or exogenous enkephalins.

(h) Amides of formula (I) as hereinbefore defined, and pharmacologically and pharmaceutically acceptable basic salts thereof, for use in the prophylaxis and/or treatment of anxiety is a mammal such as man.

(i) Amides of formula (I) as hereinbefore defined, and pharmacologically and pharmaceutically acceptable basic salts thereof, for use in the prophylaxis and/or treatment of convulsions in a mammal such as man.

(j) Amides of formula (I) as hereinbefore defined and pharmacologically and pharmaceutically acceptable basic salts thereof, for use in the prophylaxis and/or treatment of a condition of a mammal such as man where an improvement in cardio-pulmonary function is indicated.

(k) Amides of formula (I) as hereinbefore defined and pharmacologically and pharmaceutically acceptable basic salts thereof, for use in the relief of dyspnoea in a mammal such as man, e.g. that of acute left ventricular failure or pulmonary oedema.

(l) Amides of formula (I) as hereinbefore defined and pharmacologically and pharmaceutically acceptable basic salts thereof, for use in the treatment of a mammal for a condition where an agent with a morphine-like effect is indicated.

(m) Amides of formula (I) as hereinbefore defined and pharmacologically and pharmaceutically acceptable basic salts thereof, for use in the treatment of a mammal for a condition selected from those specifically identified hereinabove under (1), (2), (3), (4), (5), (6) or (7)

(n) A method for the prolongation and/or potentiation in a mammal of the effects of endogenous or exogenous enkephalins comprising administration to the mammal of a non-toxic, therapeutically effective amount of am amide of formula (I) as hereinbefore defined or a pharmacologically and pharmaceutically acceptable basic salt thereof.

(o) A method of prophylaxis and/or treatment of anxiety in a mammal, comprising administration to the mammal of a non-toxic, therapeutically effective amount of an amide of formula (I) as hereinbefore defined or a pharmacologically and pharmaceutically acceptable basic salt thereof.

(b) A method of prophylaxis and/or treatment of convulsions in a mammal, comprising administration to the mammal of a non-toxic, therapeutically effective amount of an amide of formula (I) as hereinbefore defined or a pharmacologically and pharmaceutically acceptable basic salt thereof.

(q) A method of prophylaxis and/or treatment of a mammal for a condition where an improvement in cardio-pulmonary function is indicated, comprising administration to the mammal of a non-toxic, therapeutically effective amount of an amide of formula (I) as hereinbefore defined or a pharmcologically and pharmaceutically acceptable basic salt thereof.

(r) A method for the relief of dyspnoea (e.g. that of acute left ventricular failure or pulmonary oedema) in a mammal, comprising administation to the mammal of a non-toxic, therapeutically effective amount of an amide of formula (I) as hereinbefore defined or a pharmacologically and pharmaceutically acceptable basic salt therof.

(s) A method for the treatment of a mammal for a condition where an agent with a morphine-like effect is indicated comprising administration to the mammal of a non-toxic, therapeutically effective amount of an amide of formula (I) as hereinbefore defined or a pharmacologically and pharmaceutically acceptable basic salt thereof.

(t) A method for the treatment of a mammal for a condition selected from those specifically identified hereinabove under (1), (2), (3), (4), (5), (6) or (7) comprising administration to the mammal of a non-toxic, therapeutically effective amount of am amide of formula (I) hereinbefore defined or a pharmacologically and pharmaceutically acceptable basic salt thereof.

(u) A method according to (n), (o), (p), (q), (r), (s) or (t) supra wherein the mammal is man.

The following examples are provided in illustration of the present invention and should not be construed as in any way constituting a limitation thereof. All temperatures are in degrees Celsius.

NOTES

Solvent systems for t.l.c. (Merck silica gel plates)
(1) methyl ethyl ketone
(2) chloroform: methanol: 32% ammonia (120:90:5)
(3) chloroform: methanol: 32% acetic acid (120:90:5)
(4) chloroform: methanol: 0.880 aq. ammonia (120:90:5)
(5) chloroform: methanol: 35% aq. acetic acid (120:90:5)
(6) n-butanol: acetic acid: $H_2O$ (3:1:1).

ABBREVIATIONS

HOBT = 1-hydroxybenzotriazole
DCCI = dicyclohexylcarbodiimide
THF = tetrahydrofuran
DMF = dimethylformamide
NMM = N-methylmorpholine
TFA = trifluoroacetic acid
DIPE = diisopropylether
Pd.C. = paladium charcoal catalyst
DCHA = dicyclohexylamine
DMSO = dimethylsulphoxide

EXAMPLE 1

N-[2-(N-Hydroxycarbamoyl)-3-phenylpropanoyl]-L-leucine (Compound No. 1)

(a) Monoethyl benzylmalonate

Diethyl benzylmalonate (89.5 g) was dissolved in absolute ethanol (230 ml) and a cold solution of KOH (22.06 g) in absolute ethanol (230 ml) added with stirring over a period of 1 hour. Stirring was continued at ambient temperature overnight. The mixture was concentrated in vacuo to an oil (63 g)

(b) N-(2-Ethoxycarbonyl-3-phenylpropanoyl)-L-leucine tert-butyl ester

Monoethyl benzylmalonate (11.1 g) was dissolved in DMF (100 ml), cooled to $-10°$ and 1-hydroxybenzotriazole (HOBT) (13.5 g) and dicyclohexylcarbodiimide (DCCI) (10.3 g) added. After stirring at $-10°$ C. for 40 mins, Leu.O But (9.35 g) was added and the mixture stirred at $+4°$ C. overnight. The mixture was filtered and the filtrate concentrated in vacuo.

The residue was dissolved in ether (800 ml) and washed successively with 50 ml portions of 10% NaHCO$_3$, ½ sat.NaCl, 10% citric acid and ½ sat NaCl. After drying (MgSO$_4$), the solvent was removed in vacuo and the residue crystallised from light petroleum (b.p. 60°-80°) to give colourless prisms (16.3 g) m.p. 65°-67° C.

$C_{22}H_{33}NO_5$ Requires: C, 67.52; H, 8.44; N, 3.58; Found: C, 67.25; H, 8.43; N, 3.56%.

Rf (1) 0.73 (2) 0.85 (3) 0.89; $[\alpha]_{589}^{23} = -45.8°$; $[\alpha]_{546}^{33} = -54.5°$ (C=1.2 in MeOH).

(c) N-(2-Carboxy-3-phenylpropanoyl)-L-leucine tert-butyl ester

The product of stage (b) (16.18 g) was dissolved in methanol (80 ml) and water (10 ml) and N.NaOH added, maintaining the pH at 12.2. After 2 hours the theoretical amount of alkali (41.4 ml) had been added and the mixture was concentrated in vacuo. The residue was dissolved in water (100 ml), filtered and acidified at 0° C. with 20.7 ml. 2N.HCl under ethyl acetate (150 ml). The aqueous phase was re-extracted with ethyl acetate (2×150 ml), the combined extracts washed with ½ sat NaCl (50 ml), dried (MgSO$_4$) and concentrated in vacuo. The residue crystallised on standing and was recrystallised from a mixture of ethyl acetate/light petroleum to give colourless needles (13.88 g) m.p. 78°-80° C.

$C_{20}H_{29}NO_5$ Requires: C, 66.12; H, 7.99; N, 3.86; Found: C, 66.41; H, 8.68; N, 3.69%.

Rf (1) 0.40 (3) 0.68; $[\alpha]_{589}^{23} = -65.2°$; $[\alpha]_{596}^{23} = -75.8°$ (C=0.7 in MeOH).

(d) N-[2-(N-Benzyloxycarbamoyl)-3-phenylpropanoyl]-L-leucine tert-butyl ester

The product of stage (c) (3.63 g) was dissolved in THF (25 ml) and cooled to $-20°$ C. NMM (1.01 g) was added followed by isobutylchloroformate (1.366 g). After stirring for 3 mins, a precooled solution of O-benzylhydroxylamine (3.79 g) in THF (5 ml) was added and the mixture stirred at $+4°$ C. for 6 hours. After concentrating in vacuo, the residue was dissolved in ethyl acetate (150 ml) and acid/base washed in the normal manner. After drying (MgSO$_4$) evaporation in vacuo gave an oil which crystallised on standing in light petroleum. Recrystallisation from ethyl acetate/light petroleum gave colourless prisms (2.49 g), m.p. 151°-154° C.

$C_{27}H_{36}N_2O_5$ Requires: C, 69.23; H, 7.69; N, 5.98; Found: C, 69.55; H, 7.45; N, 5.70%.

Rf (1) 0.72 (3) 0.92; $[\alpha]_{589}^{24} = -42.3°$; $[\alpha]_{546}^{24} = -58.6°$ (C=0.1 in MeOH).

(e) N-2-(N-benzyloxycarbamoyl)-3-phenylpropanoyl.-L-leucine

The product of stage (d) (2.48 g) was dissolved in TFA (70 ml) and stirred at ambient temperature for 90 mins. The solution was evaporated in vacuo and the residue crystallised on standing in DIPE to give prisms (1.86 g) m.p. 153°-156° C.

$C_{23}H_{28}N_2O_5$ Requires: C, 66.99; H, 6.80; N, 6.80; Found: C, 66.50; H, 6.90; N, 6.82%.

Rf (3) 0.75 $[\alpha]_{589}^{24} = -28.8°$; $[\alpha]_{546}^{24} = -37.8°$ (C=0.9 in MeOH).

(f) N-[2-(N-hydroxycarbamoyl)-3-phenylpropanoyl]-L-leucine

The product of stage (e) (1.85 g) was dissolved in methanol (50 g) and hydrogenated in the presence of 10% Pd.C (0.5 g). After the absorption of 92 ml. H$_2$, the catalyst was filtered and the filtrate concentrated in vacuo to give a solid which crystallized from water as colourless prisms (1.04 g) m.p. 164°-166° C.

$C_{16}H_{22}N_2O_5 \cdot 0.5H_2O$ Requires: C, 58.01; H, 6.95; N, 8.46; Found: C, 58.04; H, 6.66; N, 8.44%.

Rf (6) 0.63; $[\alpha]_{589}^{26} = -38.8°$ (C=0.5 in MeOH).

The n.m.r. was consistent with the proposed structure. The product gives an intense red colour with aqueous ferric chloride solution.

EXAMPLE 2

N-[2-(N-Hydroxycarbamoyl)-3-(4-isopropylphenyl)-propanoyl]-L-leucine (Compound No. 2)

(a) Diethyl p-isopropylbenzylmalonate

Diethyl malonate was added dropwise at 20°-25° C. to a stirred suspension of sodium hydride (1 equi) in dry DMSO. The mixture was stirred until the evolution of hydrogen had ceased (ca. 1 hour), then a solution of p-isopropylbenzyl bromide (1 equiv.) (prepared from p-isopropylbenzyl alcohol and PBr$_3$) in dry DMSO added dropwise with stirring. After stirring at room temperature for 1.5 hours the mixture was heated on the steam bath for 0.5 hour until a clear solution was obtained. The mixture was poured onto ice, extracted several times with ether and the extracts combined and washed with water and brine, dried (MgSO$_4$) and evaporated in vacuo. The residual oil was distilled, collecting the fraction b.p. 160°-170° (2-3 mm).

(b) Monoethyl p-isopropylbenzylmalonate

The product of stage (a) was saponified in ethanol with KOH as described for Example 1 to yield an oil.

(c) N-[2-Ethoxycarbonyl-3-(4-isopropylphenyl)-propanoyl]-L-leucine tert-butyl ester To a solution of the above malonate (1.1 equiv.) in THF cooled to $-25°$ C. was added NMM (1.1 equiv.) and isobutylchloroformate (1.05 equiv). After stirring for 2 min, Leu.OBu$^t$(1 equiv) in THF, recooled to $-25°$ C. was added and the mixture stirred at $-15°$ C. for 2 hours. The temperature was raised to 0° C., 2N.KHCO$_3$ (2.45 equiv) added and stirring continued at 0° C. for an additional 30 mins. The product was evaporated in vacuo, the residue dissolved in ethyl acetate and acid/base washed in the normal manner, dried and evaporated to give a solid m.p. 68°–73° C. The n.m.r. and mass spec. were consistent with the structure.

(d) N-[2-Carboxy-3-(4-isopropylphenyl)propanoyl]-L-leucine tert-butyl ester

The product of stage (c) was saponified by stirring in ethanol containing a little water with KOH (1.1 equiv). The reaction was followed by t.l.c. After 4 hours the mixture was evaporated in vacuo and the residue partitioned between water and ether. The aqueous phase was cooled to 0° C. and acidified under ether to pH 1 with 2N.HCl. The aqueous phase was re-extracted exhaustively with ether, the combined etheral extracts washed with brine, dried and evaporated. The residual oil was dissolved in ether, DCHA (1.05 equiv) added and the crystallised solid filtered. m.p. 155°–158° C.

$C_{35}H_{58}N_2O_5$ Requires: C, 71.63; H, 9.96; N, 4.77; Found: C, 71.77; H, 10.25; N, 4.77%.

The dicyclohexylamine salt was suspended in ethyl acetate and shaken twice with 5% citric acid solution. After washing the brine, and drying, the solvent was removed in vacuo.

(e) N-[2-(N-Benzyloxycarbamoyl)-3-(4-isopropylphenyl)propanoyl]-L-leucine tert-butyl ester The residue from stage (d) was stirred in DMF at −15° C. for 1 hour with HOBT (2 equiv) and DCCl (1 equiv). To the mixture was added a precooled solution of O-benzylhydroxylamine hydrochloride (1 equiv) and NMM (1 equiv) in DMF and stirring continued for 48 hour at +4° C. The product was filtered, the filtrate concentrated in vacuo, dissolved in ethyl acetate and acid/base washed in the normal manner. The solution was dried (MgSO$_4$), evaporated in vacuo and the residue used the next stage without further purification.

(f) N-[2-(N-Benzyloxycarbamoyl)-3-(4-isopropylphenyl)propanoyl]-L-leucine tert-butyl ester The product of stage (e) was stirred at ambient temperature with TFA (50 ml) for 30 mins. The solution was concentrated in vacuo and re-evaporated several times with CCl$_4$. The residue was dissolved in ether and DCHA (1.05 equiv) added. After refrigerating overnight the crystalline solid was filtered, washed with ether and dried. m.p. 195°–205° (dec)

$C_{38}H_{57}N_3O_5 1.5H_2O$ Requires: C, 68.97; H, 9.14; N, 6.35; Found: C, 68.68; H, 8.93; N, 6.09%.

(g) N-[2-(N-Hydroxycarbamoyl)-3-(4-isopropylphenyl)propanoyl]-L-leucine

The DHCA salt was hydrogenated in methanol in the presence of 10% Pd.C. After the theoretical amount of H$_2$ had been taken up (1.5 hour) the catalyst was filtered and the solvent removed in vacuo. The residue was suspended in ethyl acetate and shaken with 5% citric acid solution in the normal manner. The solution was dried and evaporated and the residue crystallised from ether as colourless prisms m.p. 173°–177° C.

$C_{19}H_{28}N_2O_5 0.5H_2O$ Requires: C, 61.11; H, 7.83; N, 7.50; Found C, 61.46; H, 7.82; N, 7.37%.

EXAMPLE 3

N-[2-(N-Hydroxycarbamoyl)-3-(4-methoxyphenyl)propanoyl]-L-leucine (Compound No. 3)

(a) N-[2-Carboxy-3-(4-methoxyphenyl)propanoyl]-L-leucine tert-butyl ester

The aove compound was prepared from p-methoxybenzyl bromide and diethyl malonate by an analogous sequence of reactions to those described in Example 1. The product was obtained as a crystaline solid m.p. 100°–105° (dec).

$C_{21}H_{31}NO_6 \frac{1}{4}H_2O$ Requires C, 63.38; H, 7.98; N, 3.42; Found: C, 63.49; H, 7.79; N, 3.35%.

(b) N-[2-(N-Hydroxycarbamoyl)-3-(4-methoxyphenyl)propanoyl]-L-leucine tert-butyl ester To a solution of the above acid in THF cooled to −25° C. was added NMM (1 equiv) and isobutylchloroformate (1.05 equiv). After 2 mins a precooled mixture of hydroxylamine hydrochloride (1.075 equiv) and NMM (1.075 equiv) in DMF was added. After stirring at −15° C. for 2 hours the product was evaporated in vacuo. The residue was dissolved in ethyl acetate, acid/base washed, dried and evaporated. The residue crystallised from acetone as colourless prisms m.p. 145°–155° C.

$C_{21}H_{32}N_2O_6 \cdot \frac{1}{4}H_2O$ Requires: C, 61.08; H, 7.94; N, 6.79; Found: C, 61.08; H, 7.67; N, 6.54%.

(c) N-[2-(N-Hydroxycarbamoyl)-3-(4-methoxyphenyl)propanoyl]-L-leucine

The product of stage (b) was cleaved from the above ester with TFA. The product crystallised from ether as prisms m.p. 161°–174° C.

$C_{17}H_{24}N_2O_6$ Requires: C, 57.94; H, 6.86; N, 7.95; Found: C, 58.23; H, 7.06; N, 7.81%.

EXAMPLE 4

Ethyl N-[(DL)-2-hydroxycarbamoyl)-3-phenylpropanoyl]-L-leucinate (Compound No. 4)

(a) N-(2-Benzoxycarbonylphenylpropanoyl)-L-leucine ethylester

To monobenzyl benzylmalonate (2.84 g)/U.S. Pat. No. 3,647,780/in DMF (25 ml) cooled to −15° C. was added HOBT (2.70 g) and DCCI (2.06 g). After 15 mins stirring at −15° C. Leu.OEt HCl (1.95 g) and triethylamine (1.38 ml) were added and the mixture stirred at +4° C. overnight. The mixture was filtered and the filtrate concentrated in vacuo to an oil. This was dissolved in ether (30 ml) and refrigerated. After filtering the small amount of precipitate the filtrate was diluted with ethyl acetate (100 ml) and washed with 30 ml portions of: ½ sat. NaCl, 10% citric acid, ½ sat. NaCl, 10% NaHCO$_3$ (2×), ½ sat. NaCl, dried (MgSO$_4$) and the solvent was removed in vacuo to give an oil (4.2 g). Rf (1) 0.68 (5) 0.92.

(b) Benzylmalonylleucine ethylester

The oil from stage (a) (4.2 g) was dissolved in ethanol (30 ml) and hydrogenated at room temperature and pressure in the presence of 10% Pd.C (0.5 g). After absorption of 229 ml $H_2$ the catalyst was filtered and the filtrate concentrated in vacuo to an oil. This oil was dissolved in water (40 ml) and 10% $NaHCO_3$ (8.5 ml) and washed with ether (2×50 ml). The aqueous phase was acidified with 2N hydrochloric acid (5 ml) and extracted into ether (2×50 ml). After drying ($MgSO_4$) the solvent was concentrated in vacuo to an oil. This dissolved in ether (40 ml) and DCHA (1.85 ml) added, the crystalline solid filtered and washed with ether, m.p. 148°-149.5° C. Yield 3.97 g.

$C_{30}H_{48}N_2O_5$ Requires: C, 69.77; H, 9.30; N, 5.43; Found: C, 69.85; H, 9.18; N, 5.35%.

(c) Ethyl N-[2-(N-Benzyloxycarbamoyl)-3-phenylpropanoyl]-L-leucinate

The dicyclohexylamine salt (above) was suspended in ethyl acetate (75 ml) and potassium hydrogen sulphate (1.5 eq.) in water (25 ml). The ethyl acetate extract was washed with water, dried and the solvent removed in vacuo.

The oil (2.58 g) was dissolved in THF (20 ml) and cooled to −28° C. N.M.M. (0.78 g) was added followed by isobutylchloroformate (1.05 g). After stirring for 3 mins, a precooled solution of O-benzylhydroxylamine hydrochloride (3.69 g) in water (10 ml) and THF (15 ml) neutralised with N.M.M. (2.33 g) was added and the mixture stirred at −15° C. for 5 h.

After concentrating in vacuo, the residue was dissolved in ethyl acetate (100 ml) and washed with 20 ml portions of 10% $NaHCO_3$, ½ sat. NaCl, 10% citric acid, ½ sat. NaCl. After drying ($MgSO_4$) evaporation in vacuo gave an oil which crystallised on standing in ether. Yield 2.35 g, M.p. 155°-162°.

$C_{25}H_{32}NO_5$ Requires: C, 68.18; H, 7.27; N, 6.36; Found: C, 68.62; H, 7.21; N, 6.36%.

Rf (1) 0.72, (5) 0.91.

(d) Ethyl N-[(DL)-2-hydroxycarbamoyl-3-phenylpropanoyl]-L-leucinate

The product from stage 3 (2.35 g) was dissolved in ethanol (50 ml) and hydrogenated in the presence of 10% Pd.C (0.5 g). After absorption of 153 ml $H_2$, the catalyst was filtered and the filtrate concentrated in vacuo to give a solid which crystallised from DIPE as colourless needles (1.30 g), m.p. 152°-155° C.

$C_{18}H_{26}N_2O_5$ Requires: C, 61.71; H, 7.43; N, 8.00; Found: C, 62.06; H, 7.75; N, 7.97%.

Rf (1) 0.58, 0.61, (5) 0.85, (4) 0.65, 0.71.

The n.m.r. was consistent with the proposed structure [Ratio of isomers present being 76:24].

EXAMPLE 5

Preparation of Methyl N-[(DL)-2-hydroxycarbamoyl-3-phenylpropanoyl]-L-leucine (Compound No. 5)

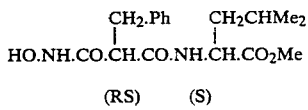

(a) Methyl-N-(2-benzoxycarbonyl-3-phenylpropanoyl)-L-leucinate

To monobenzyl benzylmalonate (2.84 g) in DMF (25 ml) cooled to −15° C. was added HOBT (2.70 g) and DCCI (2.06 g). After 20 min at −15° C., L-LeuOMe hydrochloride (1.82 g) and triethylamine (1.38 ml) were added, and the mixture stirred at +4° C. overnight. The mixture was filtered and the filtrate concentrated in vacuo to an oil. This was dissolved in ethyl acetate and refrigerated. After filtering the small amount of precipitate, the filtrate was diluted with ethyl acetate (100 ml) and washed with 30 ml portions of: ½ sat. NaCl, 10% citric acid, ½ sat. NaCl, 10% $NaHCO_3$ (2×), ½ sat. NaCl, dried ($MgSO_4$) and the solvent removed in vacuo to give an oil (3.96 g). Rf (1) 0.68, (5) 0.95.

(b) Methyl N-(2-carboxy-3-phenylpropanoyl)-L-leucinate

The oil from above (3.96 g) was dissolved in methanol (40 ml) and hydrogenated in the presence of 10% Pd.C (0.5 g). After absorption of 220 ml of $H_2$ the catalyst was filtered and the filtrate concentrated in vacuo to an oil. This was dissolved in water (40 ml) and 10% $NaHCO_3$ (12 ml) and washed twice with ether. The aqueous phase was acidified with 2N HCl (7 ml) and extracted with ether (2×50 ml).

After drying ($MgSO_4$) the solvent was removed in vacuo to give an oil (2.8 g). This was dissolved in ether (40 ml), DCHA (1.90 ml) added and the solution stirred at +4° C. overnight. The crystalline solid was filtered and washed with petrol to give a white solid with M.p. 113°-115° C. (3.84 g).

$C_{29}H_{46}N_2O_5$ Requires: C, 69.32; H, 9.16; N, 5.58; Found: C, 69.26; H, 9.52; N, 5.48%.

(c) Methyl N-[2-(N-benzyloxycarbamoyl)-3-phenylpropanoyl]-L-leucinate

The dicyclohexylamine salt above (3.84 g) was suspended in ethyl acetate (75 ml) and potassium hydrogen sulphate (1.56 g, 1.5 eq) in water (25 ml) added. The ethyl acetate extract was washed with water, dried ($MgSO_4$) and the solvent removed in vacuo to give an oil (2.45 g).

The oil was dissolved in THF (20 ml) and cooled to −20° C. N.M.M. (0.77 g) was added followed by isobutylchloroformate (1.04 g). After 3 min stirring, a precooled solution of O-benzylhydroxylamine hydrochloride (2.43 g) in water (8 ml) and THF (15 ml) neutralised with N.M.M. (1.54 g) was added and the mixture stirred at −15° C. for 5 h. After concentrating in vacuo, the residue was dissolved in ethyl acetate (150 ml) and washed with 25 ml portions of 10% $NaHCO_3$, ½ sat. NaCl, 10% citric acid (2×), ½ sat. NaCl. After drying (MgSO4) evaporation of the solvent in vacuo gave an oil which crystallised on standing in ether. Yield 1.93 g, M.p. 138°–142° C.

$C_{24}H_{30}N_2O_5$ Requires: C, 67.61; H, 7.04; N, 6.57; Found: C, 67.33; H, 7.11; N, 6.48%.

(d) Methyl N-[(DL)-2-hydroxycarbamoyl-3-phenylpropanoyl]-L-leucinate

The product from stage (c) (1.93 g) was dissolved in methanol (40 ml) and hydrogenated in the presence of 10% Pd.C (0.5 g). After absorption of 110 ml $H_2$, the catalyst was filtered and the filtrate concentrated in vacuo, to give a white crystalline solid, washed with DIPE, 1.30 g, M.p. 151°–152° C.

$C_{17}H_{24}N_2O_5$ Requires: C, 60.71; H, 7.14; N, 8.33; Found: C, 60.63; H, 7.00; N, 8.24%.

Rf (5) 0.83 (4) 0.61, 0.69, (1) 0.55, 0.60.

The n.m.r was consistent with the proposed structure [Ratio of isomers present 64:36].

EXAMPLE 6

Preparation of Tert-butyl N-[(DL)-2-hydroxycarbamoyl)-3-phenylpropanoyl]-L-leucinate (Compound No. 6)

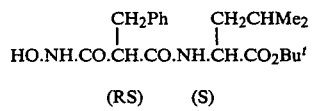

(RS)   (S)

Tert-butyl N-[(DL)-2-hydroxycarbamoyl-3-phenylpropanoyl]-L-leucinate

The product of Example 1(d) (4.27 g) was dissolved in ethanol (75 ml) and hydrogenated in the presence of 10% Pd.C (1 g). After absorption of 281 ml of $H_2$ the catalyst was filtered and the filtrate concentrated in vacuo to give a solid which crystallised from propan-2-ol/water.

Yield 2.10 g, M.p. 159°–160° C.

$C_{20}H_{30}N_2O_5$ Requires: C, 63.49; H, 7.94; N, 7.41; Found: C, 63.20; H, 8.41; N, 7.18%.

Rf (1) 0.63, (4) 0.73, (5) 0.82.

The n.m.r. was consistent with the proposed structure, ratio of isomers is 1:1.

EXAMPLE 7

Using an analogous sequence of reactions to those described in Example 1, further compounds were prepared having the general formula:

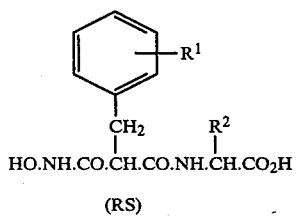

(RS)

in which the values $R^1$ and $R^2$ are as shown in the following Table:

| Compound No. | $R^1$ | $R^2$ |
|---|---|---|
| 7 | H | H |
| 8 | p-CH3 | —CH2CH(CH3)2 |
| 9 | p-NO2 | —CH2CH(CH3)2 |
| 10 | p-Br | —CH2CH(CH3)2 |

The above compounds were characterised as follows:

| Compound No. | m.p. | Elemental Analysis | |
|---|---|---|---|
| 7 | 198–199° | $C_{24}H_{37}N_3O_5$ | Requires: C, 64.43; H, 8.28; N, 9.40 Found: C, 64.56; H, 8.64; N, 8.91% |
| 8 | 135–140° | $C_{17}H_{21}N_3O_5$, ½$H_2O$, ¼$Et_2O$ | Requires: C, 58.00; H, 6.92; N, 10.68 Found: C, 58.42; H, 6.37; N, 10.89% |
| 9 | 158–163° | $C_{16}H_{21}N_3O_7$. ½$H_2O$, ¼$Et_2O$ | Requires: C, 52.29; H, 6.58; N. 10.16% Found: C, 52.64; H, 6.17; N, 10.08% |
| 10 | 164–176° | $C_{16}H_{21}N_2O_5Br$ $(CH_3)_2CO$ | Requires: C, 49.68; H, 5.92; N, 6.10 Found: C, 49.53; H, 5.80; N, 5.91% |

ACTIVITY IN VITRO

The compounds were investigated for enkephalinase inhibiting activity using the following method.

Purified enkephalinase A1 was obtained according to the following procedure (modification of the method of Gorenstein and Snyder, Life Sciences, Vol. 25, pages 2065–2070, 1979).

Rats were killed by decapitation and the striata dissected out on ice. The pooled tissues were homogenised on ice-cold Tris/hydrochloric acid buffer (50 mM, pH 7.70, 30 ml per gram of tissue) and centrifuged (50,000 g, 15 mins). The resulting supernatant was discarded and the remaining pellet washed three times. The washed pellet was solubilised by resuspension in half the volume of buffer as before containing 1.0% (v/v) Triton X-100 and incubated at 37° C. for 45 mins. The suspension was then centrifuged at 100,000 g for 60 mins and the solubilised enzymes contained in the supernatant separated by DEAE-cellulose column chromatography. Enkephalinase A1 was further purified by Sephacryl S.300 chromatograph.

Enkephalinase-inhibiting activity was estimated by the following procedure. 1.75 μl of leucine enkephalin (0.317 mg/ml), 0.5 μl of $^3H$-leucine enkephalin ([tyrosyl-3,5-$^3H$]Enkephalin (5-L-leucine). The Radiochemical Centre, Amersham, England) and 5.75 μl of buffer as before were incubated at 30° C. for 10 mins with 2 μl of either a solution of test compound (in either 50% ethanol/0.1M sodium hydrogen carbonate or distilled water) or solvent alone as control. 10 μl of purified enkephalinase A1 at 30° C. were added and incubation then continued for a further 30 mins (total incubation 40 mins, final leucine enkephalin concentration $5 \times 10^{-5}M$, final $^3H$-leucine enkephalin concentration 12.5 μCl/ml). At the completion of incubation 3 μl of 0.16M hydrochloric acid was added and the incubation mixture cooled on ice.

Separation of (a) unchanged $^3H$-leucine enkephalin and (b) $^3H$-Tyr-Gly-OH($^3H$-TGG), generated from (a)

by enkephalinase A1 in the incubation mixture was effected by thin layer chromatography (plastic silica gel plates of 0.1 mm layer thickness, solvent system ethyl acetate:propan-2-ol:5% (v/v) acetic acid, 2:2:1) using solutions of the cold compounds as carriers. After drying the materials were visualized with ninhydrin and appropriate areas of the plates cut out and placed in scintillation vials containing 50% methanol/0.1M hydrochloric acid to elute the $^3$H label. Bioflor reagent (10 ml) was then added and the radioactivity determined by liquid scintillation counting.

The $^3$H-TGG generated in the presence of test compound (expressed as a percentage of the control figure) was then calculated and an approximate IC$_{50}$ figure (concentration of compound test required for 50% inhibition of $^3$H-TGG generation) then determined graphically. For comparison purpose, the IC$_{50}$ figures for Captopril and Thiorphan are also given.

| Compound | IC$_{50}$(M) |
|---|---|
| 1 | $1.9 \times 10^{-8}$ |
| 2 | $1.2 \times 10^{-7}$ |
| 3 | $7.5 \times 10^{-7}$ |
| 7 | $1.3 \times 10^{-7}$ |
| 9 | $5.2 \times 10^{-7}$ |
| 10 | $6 \times 10^{-8}$ |
| Captopril | $3 \times 10^{-3}$ |
| Thiorphan | $1.2 \times 10^{-8}$ |

ACTIVITY EX VIVO

Mice were dosed i.p. with 0–30 mg/Kg of test compound suspended in 0.25% w/v celacol/0.85% w/v saline. The mice were killed 15 minutes after administration of the doses. The lung and brain (less cerebellum) were rapidly dissected, weighed and homogenised in 100 mM tris-HCl pH 7.4 buffer containing 1 uM Captopril to give a 9.1% W/V homogenate. 'Enkephalinase' activity in the homogenate was measured by incubation at 37° C. with 100 μM [$^3$H]-D-Tyr-D-Ala-L-Gly-L-Gly-L-Phe-L-leu for 10 minutes (lung) or 30 minutes (brain). Incubations were stopped by the addition of 1N HCl and [$^3$H]-metabolite ([$^3$H]-D-Tyr-D-Ala-L-Gly) separated from [$^3$H]-substrate by Porapak cloumn chromatography (Hudgin et al. (1981), Life Sci., 29, 2593–2601). In addition to compounds of formula (I), Thiorphan was also subjected to the same test for comparison.

The results of the tests yield 'apparent' ED$_{50}$ values for lung and brain. However, none of the compounds tested irreversibly inhibit 'enkephalinase' activity in vitro. The ED$_{50}$ values are therefore dependent on the pharmacokinetics of distribution, potency (probably reflected by potency in lung homogenates), and dissociation from enzyme during homogenisation and enzyme assay procedure. Thus the ED$_{50}$ values measured in this ex vivo assay are probably less than actual in vivo figures. The ED$_{50}$ ratios for lung and brain are also given.

| Compound | Lung | Apparent ED$_{50}$(u mol/kg) Brain | Lung/Brain |
|---|---|---|---|
| 1 | 6.1 | 14.6 | 2.4 |
| 4 | 8.6 | >85.7 | >10 |
| 6 | >26.5 | No inhibn. at 26.5 | — |
| Thiorphan | 0.69 | 3.92 | 5.68 |

PHARMACEUTICAL FORMULATIONS

The compound of formula (I) employed in the following Examples of pharmaceutical formulations may be any compound of formula (I) defined above or a basic salt thereof.

(A) Tablet Formulation (0.5 mg/tablet)

| Compound of formula | 0.5 mg |
|---|---|
| Maize Starch | 10 mg |
| Polyvinylpyrrolidone | 2 mg |
| Magnesium Stearate | 2 mg |
| Lactose | to 100 mg |

Mix together the compound of formula (I), Lactose and Maize Starch. Granulate with a solution of the Polyvinylpyrrolidone dissolved in water. Dry the granules, add the Magnesium Stearate and compress to product tablets, 100 mg per tablet.

(B) Suppository (0.5 mg/product)

| Compound of formula (I) | 25 mg |
|---|---|
| Suppository Base (Massa Esterinum C) | to 100 g |

Melt the suppository base at 40° C. Gradually incorporate the compound of formula (I) in fine powder form and mix until homogenous. Pour into suitable moulds, 2 g per mould, and allow to set. Massa Esterinum C is a commercially available suppository base consisting of a mixture of mono, di and tri-glycerides of saturated vegetable fatty acids. It is marketed by Henkel International, Dusseldorf.

(C) Pessary (0.5 mg/product)

| Compound of formula (I) | 0.5 mg |
|---|---|
| Lactose | 400 mg |
| Polyvinylpyrrolidone | 5 mg |
| Magnesium Stearate | 4.5 mg |

Mix together the compound of formula (I) and Lactose. Granulate with a solution of Polyvinylpyrrolidone in 50% aqueous ethanol. Dry the granules, add the Magnesium Stearate and compress on suitably shaped punches, 410 mg per pessary.

(D) Freeze-dried Injection 0.5 mg/vial

| Compound of formula (I) | 0.5 mg |
|---|---|
| Mannitol | 99.5 mg |
| Water for Injections to | 2.0 ml |

Dissolve the compound of formula (I) and mannitol in the Water for Injections. Sterilise the solution by passage through a membrane filter, 0.2 μm pore size, collecting the filtrate in a sterile receiver. Fill into sterile glass vials, 2 ml/vial under aseptic conditions and freeze-dry. Close the vials with sterile rubber closures secured with an aluminium seal.

The injection is reconstituted prior to administration by the addition of a convenient volume of Water for Injections or sterile saline solution.

We claim:
1. Compounds of the formula

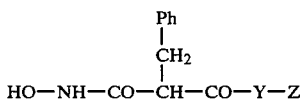

wherein Ph is phenyl substituted in the 4-position by isopropyl, methoxy, nitro or bromo; Y is a group of formula

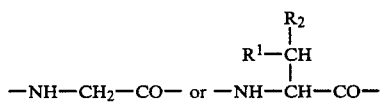

where $R^1$ is hydrogen or methyl; $R^2$ is alkyl of 1 to 3 carbon atoms or is methylthiomethyl; and Z is $-OR^3$ or $-NR^4R^5$ where $R^4$ and $R^5$ are each hydrogen or alkyl of 1 to 4 carbon atoms and $R^3$ is hydrogen, alkyl of 1 to 4 carbon atoms, phenyl alkyl of 1 to 4 carbon atoms in the alkylene moiety thereof, or phenyl and basic salts thereof.

2. Compounds as claimed in 1, wherein Y is a group of formula

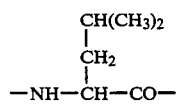

(in either the D- or the L-configuration).

3. Compounds as claimed in 1, wherein y is a group of formula

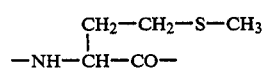

(in either the D- or the L-configuration).

4. Compounds as claimed in 1, wherein Y is a group of formula $-NH-CH_2CO-$.

5. Compounds as claimed in 1, wherein Z is $-OR^3$, where $R^3$ is an ethyl, methyl, n-propyl, isopropyl, n-butyl, isobutyl or t-butyl group.

6. Compounds as claimed in 1 wherein Z is $-OR^3$, where $R^3$ is an ethyl, methyl or t-butyl group.

7. Compounds as claimed in 1, wherein Z is $-OR^3$, where $R^3$ is hydrogen.

8. N-[2-(N-Hydroxycarbamoyl)-3-(4-isopropylphenyl)propanoyl]-L-leucine and basic salts thereof.

9. N-[2-(N-Hydroxycarbamoyl)-3-(4-methoxyphenyl)-propanoyl]-L-leucine and basic salts thereof.

10. N-[2-(N-Hydroxycarbamoyl)-3-(4-methylphenyl)propanoyl]-L-leucine and basic salts thereof.

11. N-[2-(N-Hydroxycarbamoyl)-3-(4-nitrophenyl)-propanoyl]-L-leucine and basic salts thereof.

12. N-[2-(N-Hydroxycarbamoyl)-3-(4-bromophenyl)-propanoyl]-L-leucine and basic salts thereof.

13. A method for the prolongation and/or potentiation in a mammal, of the effects of endogenous or exogenous enkephalins, comprising administration to the mammal of a non-toxic, therapeutically effective amount of a compound of formula (1),

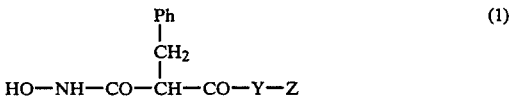

wherein Ph is a phenyl group which is optionally substituted by one or more substituents selected from halo (ie fluoro, chloro, bromo or iodo), $C_{1-4}$ alkyl, amino, $C_{1-4}$ alkylamino, di-$C_{1-4}$alkylamino, nitro, sulphonyl, aminosulphonyl, trihalomethyl, carboxy, $C_{1-4}$alkoxycarbonyl, amido, $C_{1-4}$alkylamido, $C_{1-4}$alkoxy, $C_{2-4}$alkenyl, cyano, aminomethyl or methylsulphonyl;

Y is a group formula

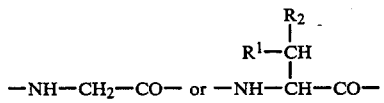

where $R^1$ is hydrogen or methyl;

$R^2$ is alkyl of 1 to 3 carbon atoms or is methylthiomethyl; and

Z is $-OR^3$ or $-NR^4R^5$ where $R^3$, $R^4$ and $R^5$ are each hydrogen or alkyl of 1 to 4 carbon atoms and $R^3$ can further be phenylalkyl having 1 to 3 atoms in the alkylene moiety thereof, or phenyl or a pharmacologically and pharmaceutically acceptable basic salt thereof.

* * * * *